United States Patent [19]

Hershberger

[11] Patent Number: 4,587,218

[45] Date of Patent: May 6, 1986

[54] NOVEL BIOCONVERTING MICROORGANISMS

[75] Inventor: Charles L. Hershberger, New Palestine, Ind.

[73] Assignee: Eli Lilly and Company, Indianapolis, Ind.

[21] Appl. No.: 544,337

[22] Filed: Oct. 21, 1983

[51] Int. Cl.$^4$ .............. C12N 1/20; C12P 21/00; C12P 21/02; C12R 1/045
[52] U.S. Cl. ...................................... 435/253; 435/68; 435/70; 435/827
[58] Field of Search ............. 435/253, 827, 68, 70

[56] References Cited

U.S. PATENT DOCUMENTS 4,064,233  12/1977  Hamill et al. ................... 424/118
4,375,513  3/1983  Debono et al. .................. 435/169

*Primary Examiner*—Thomas G. Wiseman
*Assistant Examiner*—Jayme A. Huleatt
*Attorney, Agent, or Firm*—Nancy J. Harrison; Arthur R. Whale

[57] ABSTRACT

New *Actinoplanes missouriensis* strains CUC 014 (NRRL 15647) and CSV 558 (NRRL 15646) which operate together to cosynthesize the useful glycopeptide antibiotic CUC/CSV.

4 Claims, No Drawings

NOVEL BIOCONVERTING MICROORGANISMS

SUMMARY OF THE INVENTION

This invention provides two new strains of *Actinoplanes missouriensis* which operate together to cosynthesize a new glycopeptide antibiotic called CUC/CSV. In addition, each strain can be used separately to bioconvert actaplanin factor A to the new CUC/CSV antibiotic. Antibiotic CUC/CSV has formula 1:

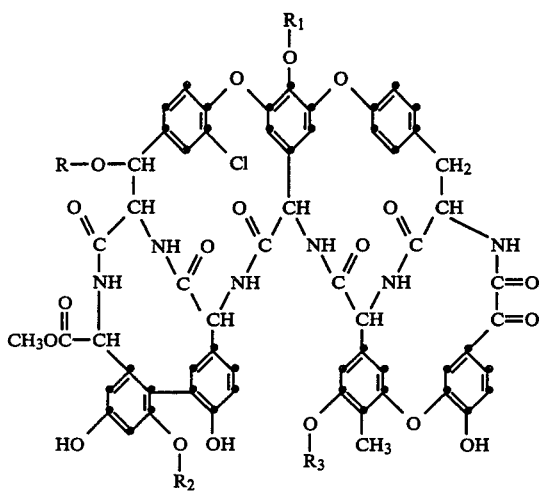

wherein

R is L-ristosaminyl;

$R_1$ is the disaccharide mannosyl-glycosyl; and $R_2$ and $R_3$ are mannosyl. CUC/CSV and its salts, particularly the pharmaceutically acceptable salts, are useful new antibiotics.

DETAILED DESCRIPTION OF THE INVENTION

This invention relates to two *Actinoplanes missouriensis* strains which together co-synthesize a new glycopeptide antibiotic and which independently are useful in certain bioconversion reactions. More particularly, the *Actinoplanes missouriensis* strains of this invention have the ability to co-synthesize the formula 1 glycopeptide antibiotic which has been designated CUC/CSV. The formula 1 compound is the subject of a co-pending application of LaVerne D. Boeck, Gladys M. Clem, Charles L. Hershberger, Marie T. Anderson and Karl H. Michel entitled GLYCOPEPTIDE COMPOUND CUC/CSV AND PROCESS FOR ITS PRODUCTION, Ser. No. 544,338, now U.S. Pat. No. 4,537,715, filed herewith this even date.

The novel *Actinoplanes missouriensis* strains of this invention have been arbitrarily designated CUC 014 and CSV 558. Cultures CSV 558 and CUC 014 are strains obtained by chemical mutagenesis of *Actinoplanes missouriensis* ATCC 31683, a strain which produces the glycopeptide antibiotic actaplanin. *A. missouriensis* ATCC 31683 in turn was derived by a series of mutations from the wild type *A. missouriensis* ATCC 23342 strain.

The glycopeptide antibiotic actaplanin (which is also known as antibiotic A4696) and the *A. missouriensis* strain ATCC 23342 are described by Hamill et al. in U.S. Pat. Nos. 3,952,095 and 4,115,552. The actaplanin-producing *A. missouriensis* strains ATCC 32680, ATCC 31682 and ATCC 31683 are described by Debono et al. in U.S. Pat. Nos. 4,322,406 and 4,375,513.

The novel *A. missouriensis* strains CSV 558 and CUC 014 of this invention do not produce actaplanin in any measurable quantity. Instead, strain CUC 014 secretes an intermediate which is then converted by strain CSV 558 to give the formula 1 compound.

CHARACTERIZATION OF CULTURES CSV 558 AND CUC 014

The following taxonomic study of the new CSV 558 and CUC 014 cultures were made together with the parent ATCC 31683 and wild type ATCC 23342 strains in order to provide a complete evaluation.

Cultures CSV 558 and CUC 014 are also classified as strains of *Actinoplanes missouriensis*. In classifying the cultures as strains of *A. missouriensis*, the methods recommended for the International Streptomyces Project (ISP) for the characterization of Streptomyces species [E. B. Shirling and D. Gottlieb, "Methods of Characterization of Streptomyces species," *Int. J. Syst. Bacteriol.* 16(3), 313–340 (1966)] and certain supplementary tests were followed.

Carbon utilization was determined with ISP No. 9 basal medium to which filter-sterilized carbon sources were added to equal a final concentration of 1.0 percent. Plates were incubated at 30° C. and read after 14 days.

Melanoid pigment production (chromogenicity) was determined with ISP No. 1 (tryptone-yeast extract broth), ISP No. 6 (peptone-yeast extract iron agar), ISP No. 7 (tyrosine agar) and modified ISP No. 7 (which lacks tyrosine).

Hydrogen sulfide production was checked by inserting test strips (Bacto H2S test strips) in ISP No. 6 agar slants.

Starch hydrolysis was determined by testing for the presence of starch with iodine on ISP No. 4 (inorganic salts-starch agar) plates (D. J. Blazevic and G. M. Ederer, "Principles of Biochemical Tests in Diagnostic Microbiology," John Wiley and Sons, Inc., New York, 1975, p. 136).

Temperature range, NaCl and sucrose tolerances, pH range, and antibiotic sensitivity were determined using ISP No. 2 (yeast-malt extract agar) plates. Plates were incubated at 30° C. for 14 days. The temperatures tested were 5°, 10°, 15°, 20°, 25°, 30°, 37°, 40°, 45°, 50° and 55° C.

NaCl tolerance was measured by adding NaCl to the agar to equal: 0, 2, 4, 6, 8, 10, and 12%; sucrose tolerance was measured by adding sucrose to equal: 0, 2, 4, 6, 8, 10, 12, 15 and 20%. The pH range was determined using the following buffers at 0.05M: citric acid, pH 3, 4, 5; 2(N-morpholino)ethanesulfonic acid (MES, Sigma Chemical Co.), pH 6; 3(N-morpholino)propanesulfonic acid (MOPS, Aldrich Chemical Co.), pH 7; N-[tris-(hydroxymethyl)methyl]glycine (Tricine, CalBiochem), pH 8; 2-(cyclohexylamino)ethanesulfonic acid (CHES, P-L Biochemicals, Inc.), pH 8.5, 9.0, and 9.5; 3-cyclohexylamino-1,1-propanesulfonic acid (CAPS), pH 10.0 and 10.5. The pH values of the agar plates were measured with a flat surface electrode prior to inoculation, and this pH was taken as the correct value. Some of the buffers failed to hold their adjusted pH. Toxicity was tested by adjusting all the buffers to pH 7.0 and checking for growth. All the mutants are sensitive to citric acid, but the wild-type strain was not sensitive to citric acid.

Antibiotic sensitivity was determined using sensitivity discs padded on the surface of seeded agar plates. The following antibiotics were used: cephalothin (sodium) 30 μg, erythromycin (estolate) 15 μg, chloromycetin 30 μg, novobiocin 30 μg, penicillin (G) 10 units, rifampin 5 μg, streptomycin 10 μg, tetracycline 30 μg and vancomycin 30 μg.

For enzyme assays the methods of Blazevic and Ederer were followed (D. J. Blazevic and G. M. Ederer, "Principles of Biochemical Tests in Diagnostic Microbiology," John Wiley and Sons, Inc., New York, 1975).

Color names were assigned using ISCC-NBC Centroid Color Charts, standard sample No. 2106 (K. L. Kelly and D. B. Judd, U.S. Dept. of Commerce, National Bureau of Standards, Washington, D.C. 20234, 1976).

Lysozyme resistance and decomposition of casein, esculin, hypoxanthine, tyrosine, and xanthine were measured by the procedure of Berg [David Berg, "Laboratory Identification of Clinically Important Aerobic Actinomycetes," *Appl. Microbiol.* 25:665–681 (1973)].

CULTURAL CHARACTERISTICS

Growth and cultural features of the four strains are similar. Only substrate, or primary, mycelia are produced. Neither secondary mycelia nor sporangia were observed on any of the fourteen agar-plating media used in the study. Sporangical descriptions of the original isolate were previously reported by Dr. John N. Couch, University of North Carolina.

The mutant strains (ATCC 31683, CSV 558 and CUC 014) produce a yellowish gray colony and are readily distinguished from the wild type (ATCC 23342), which produces a distinctive orange pigmentation ranging from moderate to brownish-orange to strong orange, depending on the medium. The mutant strains are indistinguishable on most agar plating media. Cultural differences between these strains are as follows: CUC 014 produces a strong reddish-brown soluble pigment on certain media. This is observed on yeast-malt extract agar (ISP No. 2), glycerol-asparagine agar (ISP No. 5) and tyrosine agar (ISP No. 7). CSV 558 is unable to grow on tomato paste-oatmeal agar (TPO), while ATCC 31683 and CUC 014 grow very well. This information is summarized in Table I.

TABLE I

Cultural characteristics of *Actinoplanes missouriensis* Strains[a, b].

| | ATCC 23342 | ATCC 31683 | CSV 558 | CUC 014 |
|---|---|---|---|---|
| ISP 2 | | | | |
| G | good | good | good | good |
| R | 53.m.O | 90.gy.Y | 90.gy.y | 90.gy.Y |
| Am | none | none | none | none |
| Sp | none | none | none | r brown |
| ISP 3 | | | | |
| G | poor | good | fair | fair |
| R | 76.1.yBr | 93.yGray | 93.yGray | 93.yGray |
| Am | none | none | none | none |
| Sp | none | none | none | none |
| ISP 4 | | | | |
| G | abundant | good | fair | fair |
| R | 50.s.O | 79.1.gy.yBr | 93.yGray | 93.yGray |
| Am | none | none | none | none |
| Sp | none | none | none | none |
| ISP 5 | | | | |
| G | fair | fair (dull) | good | good |
| R | 68.s.OY | 90.gy.Y | 90.gy.Y | 63.1.brGy |
| Am | none | none | none | none |
| Sp | none | none | none | l.r. gray |
| ISP 7 | | | | |
| G | poor | fair | good | good |
| R | 54.brO | 80.gy.yBr | 80.gy.yBr | 80.gy.yBr |
| Am | none | none | none | none |
| Sp | reddish br | light brown | none | d.r. brown |
| Bennetts | | | | |
| G | abundant | abundant | good | good |
| R | 53.m.O | 93.yGray | 93.yGray | 93.yGray |
| Am | none | none | none | none |
| Sp | none | none | none | l.r. brown |
| calcium malate | | | | |
| G | good (shiny) | good (shiny) | fair | fair |
| R | 50.s.O | 93.yGray | 93.yGray | 93.yGray |
| Am | none | none | none | none |
| Sp | none | none | none | none |
| Czapek's | | | | |
| G | good | abundant | good | good |
| R | 71.m.OY | 93.yGray | 93.yGray | 93.yGray |
| Am | none | none | none | none |
| Sp | none | none | none | none |
| Glucose Asparagine | | | | |
| G | good | good | none | none |
| R | 71.m.OY | 93.yGray | none | none |
| Am | none | none | none | none |
| Sp | none | none | none | none |
| TPO | | | | |
| G | good | good | none | abundant |
| R | 55.s.Br | 91.d.gy.Y | none | 91.d.gy.Y |
| Am | none | none | none | none |
| Sp | faint rBr | none | none | none |
| Anio-Hensens | | | | |
| G | poor | fair | fair | fair |
| R | 70.1.OY | 91.d.gy.Y | 93.yGray | 93.yGray |
| Am | none | none | none | none |
| Sp | none | none | none | none |
| 53H medium[c] | | | | |
| G | fair | good | fair | fair |
| R | 54.brO | 91.d.gy.Y | 93.yGray | 93.yGray |
| Am | none | none | none | none |
| Sp | none | none | none | l.r. brown |
| Czapek's Peptone | | | | |
| G | abundant | abundant | abundant | abundant |
| R | 54.brO | 90.gy.Y | 90.gy.Y | 90.gy.Y |
| Am | none | none | none | none |
| Sp | none | none | none | none |

[a]G = growth; R = reverse; Am = aerial mycelium; Sp = soluble pigment
[b]Strains incubated 14 days at 30° C.
[c]Medium 53H has the following composition (pH adjusted to 7.0):

| Ingredient | Amount |
|---|---|
| Yeast extract | 2.0 g |
| CaCO$_3$ | 3.0 g |
| Na$_2$S$_2$O$_3$.5H$_2$O | 0.5 g |
| V-8 Juice | 200.0 ml |
| Deionized H$_2$O | 800.0 ml |
| Agar | 20.0 g |

Morphological Characteristics

None of the cultures produce aerial hyphae or sporangia. Consequently, the only morphological comparisons were those made with substrate mycelia. The morphology of the primary hyphae is indistinguishable.

Physiological Characteristics

Cultures ATCC 23342, ATCC 31683, CSV 558 and CUC 014 were tested for sensitivity to nine antibiotics. They exhibited an identical pattern of sensitivity. Resistance was shown to novobiocin and penicillin G. Sensitivity was shown to cephalotin, chloromycetin, erythromycin, rifampin, streptomycin, tetracycline, and vancomycin. The test results are summarized in Table II.

TABLE II

Antibiotic Sensitivity of Actinoplanes missouriensis strains.

| Antibiotic | Conc. | ATCC 23342 | ATCC 31683 | CSV 558 | CUC 014 |
|---|---|---|---|---|---|
| Cephalothin | 30 μg | + | + | + | + |
| Chloromycetin | 30 μg | + | + | + | + |
| Erythromycin | 15 μg | + | + | + | + |
| Novobiocin | 30 μg | − | − | − | − |
| Penicillin G | 10 units | − | − | − | − |
| Rifampin | 5 μg | + | + | + | + |
| Streptomycin | 10 μg | + | + | + | + |
| Tetracycline | 30 μg | + | + | + | + |
| Vancomycin | 30 μg | + | + | + | + |

+ = sensitive (zone of inhibition)
− = resistant (no zone inhibition)

Carbon utilization is identical for CSV 558 and CUC 014. ATCC 23342 differs in salicin utilization, and ATCC 31683 differs in ribose utilization. These test results are summarized in Table III.

TABLE III

Carbon Utilization of Actinoplanes missouriensis Strains

| Carbon Source | ATCC 23342 | ATCC 31683 | CSV 558 | CUC 014 |
|---|---|---|---|---|
| no carbon | − | − | − | − |
| glucose | ++ | ++ | ++ | ++ |
| L-arabinose | ++ | ++ | ++ | ++ |
| cellobiose | ++ | ++ | ++ | ++ |
| D-fructose | ++ | ++ | ++ | ++ |
| D-galactose | ++ | ++ | ++ | ++ |
| i-inositol | − | − | − | − |
| D-mannitol | ++ | + | ++ | ++ |
| melibiose | + | + | + | ++ |
| raffinose | − | − | − | − |
| D-rhamnose | ++ | + | ++ | ++ |
| D-ribose | − | (+) | − | − |
| salicin | + | − | − | − |
| sucrose | ++ | (+) | ++ | ++ |
| D-xylose | ++ | ++ | ++ | ++ |

++ = equal to or >glucose control; positive utilization
+ = <glucose control, >no carbon control; positive utilization
(+) = growth questionable; doubtful utilization
− = no growth; negative utilization Physiological differences between CSV 558 and CUC 104 are: tolerance to sucrose, temperature range, and the degree of gelatin liquefaction. CSV 558 tolerates up to 12% sucrose, grows in a temperature range of 5°–30° C., and liquefies gelatin about 50% after 14 days incubation 30° C. CUC 014 tolerates up to 15% sucrose, grows in a temperature range of 5°–37° C., and liquefies gelatin about 80% after 14 days incubation at 30° C. These differences, as well as additional physiological characteristics for all four strains, are given in Table IV.

TABLE IV

Additional Physiological Characteristics of Actinoplanes missouriensis Strains

| Characteristic | ATCC 23342 | ATCC 31683 | CSV 558 | CUC 014 |
|---|---|---|---|---|
| casein decomposition | + | + | + | + |
| catalase reaction | + | + | + | + |
| esculin decomposition | + | + | + | + |
| gelatin liquefaction | +(40%) | +(100%) | +(50%) | +(80%) |
| H₂S production | tr | tr | tr | tr |
| hypoxanthine decomp. | − | − | − | − |
| lysozyme resistance | − | − | − | − |
| melanoid pigments | − | − | − | − |
| NaCl tolerance | <2% | <2% | <2% | <2% |
| nitrate reduction | − | − | − | − |
| pH growth range | 6–7 | 6–8.4 | 6–8 | 6–8 |
| phosphatase production | + | + | + | + |
| skim milk | − | − | − | − |
| starch hydrolysis | + | − | + | + |
| sucrose tolerance | 15% | 20% | 12% | 15% |
| temp. growth range | 15–37° C. | 5–40° C. | 5–30° C. | 5–37° C. |
| tyrosine decomposition | − | + | − | − |
| urease production | + | − | + | + |
| xanthine decomposition | − | − | − | − |

The Actinoplanes missouriensis strains CUC 014 and CSV 558 of this invention have been deposited and made part of the stock culture collection of the Northern Regional Research Center, Agricultural Research, North Central Region, 1815 North University Street, Peoria, Ill., 61604, from which they are available to the public under the accession numbers NRRL 15647 (CUC 014) and NRRL 15646 (CSV 558).

As is true with other organisms, the characteristics of the Actinoplanes missouriensis NRRL 15646 and NRRL 15647 strains are subject to variation. For example, recombinants, mutants or artificial variants of the strains may be obtained by treatment with various known physical and chemical mutagens, such as ultraviolet light, X-rays, gamma rays, and N-methyl-N'-nitro-N-nitrosoquanidine. All natural and artificial variants, mutants and recombinants of the A. missouriensis NRRL 15646 and NRRL 15647 strains which retain the ability to cosynthesize CUC/CSV may be used in this invention.

Cosynthesis of antibiotic CUC/CSV is achieved by fermenting the secretor culture CUC 014 (NRRL 15647) and the converter culture CSV 558 (NRRL 15646) together under submerged aerobic conditions in a suitable culture medium until substantial antibiotic activity is produced. When fermented separately, neither culture CUC 014 nor CSV 558 produces antibiotic activity.

As will be appreciated by those in the art, the culture media used to grow the cosynthesizing A. missouriensis strains can be any one of a number of media (see, for example, U.S. Pat. No. 4,322,406 for a description of the media variations useful for the parent A. missouriensis ATCC 31683 strain). When cosynthesizing antibiotic CUC/CSV, the fermentation can be carried out by inoculating a common medium with the two cultures simultaneously. Alternatively, a growing culture of A. missouriensis CUC 014 can be established, and then combined with a growing culture of the CSV 558 strain.

Antibiotic production can be followed during the fermentation by testing samples of the broth against organisms known to be sensitive to this antibiotic. One useful assay organism is Bacillus subtilis. The bioassay is conveniently performed by paper-disc assay on agar plates. In addition, antibiotic production can be monitored by high performance liquid chromatography (HPLC) with UV detection.

Following its production under submerged aerobic fermentation conditions, antibiotic CUC/CSV can be recovered from the fermentation medium by methods recognized in the art, e.g. adsorptive and extractive procedures.

Antibiotic CUC/CSV can also be prepared by bioconversion of actaplanin factor A using either culture CUC 014 or culture CSV 558 (see the co-pending application of Gladys M. Clem, LaVerne D. Boeck, Marie T. Anderson, and Karl H. Michel entitled GLYCOPEPTIDE BIOCONVERSION PRODUCTS, Ser. No. 544,332, now abandoned, filed herewith this even date).

Antibiotic CUC/CSV inhibits the growth of pathogenic bacteria, especially gram-positive bacteria. Table V summarizes the minimal and inhibitory concentrations (MIC's) at which CUC/CSV inhibits certain organisms, as determined by standard agar-dilution assays.

TABLE V

In Vitro Activity of CUC/CSV

| Organism | MIC (mg/ml) |
|---|---|
| Staphylococcus aureus NRRL B313 | 8 |
| Staphylococcus aureus V41 | 8 |
| Staphylococcus aureus X400 | 16 |
| Staphylococcus aureus S13E | 8 |
| Staphylococcus epidermidis EP11 | 16 |
| Staphylococcus epidermidis 222 | 8 |
| Streptococcus pneumoniae Park 1 | 0.5 |
| Streptococcus faecium ATCC 9790 | 4 |
| Streptococcus sp. group D 9960 | 4 |

Antibiotic CUC/CSV also inhibits the growth of anaerobic bacteria. Table VI summarizes the susceptibility of various anaerobic isolates to CUC/CSV.

TABLE VI

Susceptibility of Anaerobic Bacterial Isolates to CUC/CSV

| Anaerobic Bacteria | MIC ($\mu$g/ml)$^a$ |
|---|---|
| Clostridium difficile 2994 | 1 |
| Clostridium perfringens 81 | 4 |
| Clostridium septicum 1128 | 4 |
| Eubacterium aerofaciens 1235 | 2 |
| Peptococcus asaccharolyticus 1302 | 4 |
| Peptococcus prevoti 1281 | 8 |
| Peptostreptococcus anaerobius 1428 | 2 |
| Peptostreptococcus intermedium 1264 | 4 |
| Propionibacterium acnes 79 | 1 |
| Bacteroides fragilis 111 | >128 |
| Bacteroides fragilis 1877 | >128 |
| Bacteroides fragilis 1936B | >128 |
| Bacteroides thetaiotaomicron 1438 | >128 |
| Bacteroides melaninogenicus 1856/28 | >128 |
| Bacteroides melaninogenicus 2736 | 16 |
| Bacteroides vulgatis 1211 | >128 |
| Bacteroides corrodens 1874 | >128 |
| Fusobacterium symbiosum 1470 | >128 |
| Fusobacterium necrophorum 6054A | 2 |

$^a$MIC's were determined by the agar-dilution method; endpoints were read after 24-hours incubation.

CUC/CSV has also shown in vivo antimicrobial activity against experimentally-induced bacterial administered to experimentally infected mice, the activity observed was measured as an ED$_{50}$ value [effective dose in mg/kg to protect 50% of the test animals: see Warren Wick et al., J. Bacteriol. 81, 233-235 (1961)]. ED$_{50}$ values observed for CUC/CSV are given in Table VII.

TABLE VII

| ED$_{50}$ Values for CUC/CSV in Mice | |
|---|---|
| Infecting Organism | ED$_{50}$ (mg/kg/2)$^a$ |
| Staphylococcus aureus | 1.59 |
| Streptococcus pyogenes | 1.09 |

TABLE VII-continued

| ED$_{50}$ Values for CUC/CSV in Mice | |
|---|---|
| Infecting Organism | ED$_{50}$ (mg/kg/2)$^a$ |
| Streptococcus pneumoniae | 0.84 |

$^a$administered subcutaneously 1 and 4 hours post-infection

The following examples illustrate this invention.

EXAMPLE 1

Production of Antibiotic CUC/CSV by Cofermentation of Cultures CUC 014 and CSV 558

A. Shake-Flask Fermentation of Cultures CUC 014 and CSV 558

A lyophilized pellet of *Actinoplanes missouriensis* strain CUC 014 (NRRL 15647) or strain CSV 558 (NRRL 15646) is dissolved in 1-2 ml of sterilized water. This suspension is used to inoculate an agar slant having the following composition:

| Ingredient | Amount (%) |
|---|---|
| Precooked Oatmeal | 6.0 |
| Yeast | 0.25 |
| K$_2$HPO$_4$ | 0.1 |
| Czapek Mineral Stock$^a$ | 0.5 |
| Agar$^b$ | 2.5 |
| Deionized H$_2$O | q.s. to 100% |
| Unadjusted pH = 6.2; adjust to pH 7.3 with 5N NaOH; after sterilization pH = 6.7. | |

$^a$Czapek Mineral Stock:

| Ingredient | Amount (%) |
|---|---|
| KCl | 10.0 |
| MgSO$_4$.7 H$_2$O | 10.0 |
| FeSO$_4$.7 H$_2$O | 0.2 (dissolved in 2 ml of Conc. HCl) |
| Deionized water | q.s. to 100% |

$^b$Difco Laboratories

The inoculated slant is incubated at 30° C. for about eight to ten days. The mature slant culture is scraped with the serrated edge of a sterile loop to mascerate and loosen the mycelial mat. About one-fourth of the loosened mat is used to inoculate 50 ml of a vegetative medium having the following composition:

| Ingredient | Amount (%) |
|---|---|
| Glucose | 2.0 |
| Tryptone$^a$ | 0.5 |
| Yeast Extract | 0.5 |
| Tap H$_2$O | q.s. to 100% |
| Before sterilization, pH = 6.5; adjust to pH 7.2 with 5N NaOH; after sterilization, pH = 6.9; | |

$^a$Bacto Tryptone, Difco

The inoculated vegetative medium is incubated in a 250-ml Erlenmeyer flask at 30° C. for about 72 hours on a rotary shaker with a two-inch throw at 250 RPM.

Vegetative cultures can be initiated with agar-slant cultures, with lyophilized pellets of the culture (one lyophile per 50 ml of media in a 250-ml flask) and with cultures preserved in liquid nitrogen (0.8% inoculum).

Incubated vegetative medium (5%, volume/volume) is used to inoculate 50 ml of a production medium having the following composition:

| Ingredient | Amount (%) |
|---|---|
| Glucose | 2.5 |
| Corn Starch | 3.5 |

-continued

| Ingredient | Amount (%) |
| --- | --- |
| Blackstrap Molasses | 1.5 |
| Glycerol | 1.5 |
| Yeast | 2.0 |
| $K_2HPO_4$ | 0.05 |
| $(NH_4)_2SO_4$ | 0.025 |
| $CaCO_3$ | 0.2 |
| Tap $H_2O$ | q.s. to 100% |
| Before sterilization pH = 6.5; adjust to 6.8; after sterilization pH = 6.5. | |

The inoculated production medium in incubated in a 250 ml Erlenmeyer flask at 30° C. for 72 hours on a 2-inch rotary shaker at 250 RPM.

B. Cosynthesis of Antibiotic CUC/CSV

After cultures CUC 014 and CSV 558 have fermented for 72 hours separately, equal volumes of whole broth from each fermentation are combined aseptically in a sterile flask. The flasks are incubated at 30° C. on a rotary shaker for an additional 96 hours.

C. Assay for Antibiotic CUC/CSV

Whole broth (adjusted to pH 10.5) is centrifuged. The supernatant is readjusted to pH 7.0. Samples thus prepared are assayed by a *Bacillus subtilis* plate assay and by thin-layer chromatography using silics-gel plates (Merck, pre-coated plastic sheets; silica gel 60, without fluorescent indicator) and an acetone:water:ammonia (160:40:1) solvent system. Detection way by bioautography using *B. subtilis* in a minimal growth medium and incubating plates at 37° C. for about 18 hours.

EXAMPLE 2

Isolation of Antibiotic CUC/CSV

Three lots of whole fermentation broth, prepared using procedures like that of Example 1, were combined (total volume=45 L.). This broth was centrifuged using a Cepa centrifuge. The mycelia were extracted twice with water which had been adjusted to pH 10.5 with sodium hydroxide. The extracts were combined (24 L.), adjusted to pH 7.0 with hydrochloric acid and applied to a column containing 4.0 L. of Diaion HP-20 (Mitsubishi Chemical Industries, Limited, Tokyo, Japan) at a flow rate of 160 ml/minute. The column was washed successively with 8 L. of water and 12 L. of methanol:water (1:3) and then was eluted with 8 L. of methanol:water (1:1), 8 L. of methanol:water (3:1), and 20 L. of methanol, collecting 4-L fractions. Each fraction was analyzed for biological activity. The bioassay was performed by a paper-disc assay on agar plates seeded with *Bacillus subtilis*. Fractions containing the desired activity were combined, concentrated under reduced pressure and lyophilized to give 10.0 g. of crude material.

A portion of this material (0.5 g) was dissolved in 10 ml of methanol:waer (3:2) and filtered. The filtrate was applied to a 5.2-×41-cm Michel-Miller HPLPLC glass column packed with 590 ml of 25–40 micron Lichroprep RP-18 reversed-phase silica gel from MC/B Manufacturing Chemist, Inc., Cincinnati, OH. The column was eluted with (35:65) methanol:potassium dihydrogen phosphate buffer (0.05M adjusted to pH 3.5 with phosphoric acid) at a rate of 10 ml/minute, collecting 20-ml fractions. The eluate was monitored at 280 nm using an Isco Model UA-5 UV monitor with a Type 6 optical unit (Instrumentation Specialties Co., Lincoln, NE). All fractions were analyzed by padding paper disks on agar plates containing a minimal media seeded with *Bacillus subtilis*. Fractions having the desired activity were combined, adjusted to pH 7.0 with sodium hydroxide and concentrated under reduced pressure. The concentrated pool (100 ml) was applied to a column packed with 90 ml of Diaion HP-20. The column was washed with 400 ml of water and then eluted with acetonitrile:water (4:1). The first eluate (29 ml) was discarded, and the next eluate (15 ml) was collected, concentrated under reduced pressure and lyophilized to give 27 mg of pure antibiotic CUC/CSV. CUC/CSV has the following characteristics:

| | Elemental Analysis | | |
| --- | --- | --- | --- |
| | Calc.[a] | Found | |
| C—90 | 49.46 | 49.28 | |
| H—98 | 5.63 | 4.35 | |
| N—7 | 4.49 | 4.55 | |
| O—41 | 38.80 | 39.82 | (by difference) |
| Cl—1 | 1.62 | 2.00 | |

[a]For $C_{90}H_{98}N_7O_{41} \cdot 12H_2O$

Ultraviolet Absorption (in methanol):
$\lambda_{max}$ 278 nm, acid ($\epsilon \sim 17{,}000$)
$\lambda_{max}$ 277 nm, 361 nm, neutral ($\epsilon \sim 18{,}000, 9{,}000$)
$\lambda_{max}$ 295 nm, 340 nm, base ($\epsilon \sim 21{,}000, 14{,}500$)
Calculated on a molecular weight of 1200. The compound shows end-absorption at 230 nm.

Solubility: soluble in dimethyl sulfoxide, dimethylformamide, acetonitrile:water, and alcohol:water mixtures.

Mass Spectrometry (Fast Atom Bombardment): FAB MS indicates a molecular weight of 1968.

EXAMPLE 3

Preparation of CUC/CSV by Bioconversion of Actaplanin Factor A with Culture CSV 558

A. The Bioconversion

Actaplanin factor A (100 mg) is dissolved in water, sterilized by filtration, and added (final conc. of 0.3 mg/ml) to a five-day-old, one-liter fermentation of the convertor culture *A. missouriensis* CSV 558 (NRRL 15646). The fermentation is incubated an additional 48 hours. The pH of the whole broth is adjusted to 10.5 with NaOH; the broth is centrifuged, and the centrate is neutralized with HCl.

B. Isolation of CUC/CSV

A bioconversion was carried out using the procedure of Sect. A. The broth was removed by filtration, and the mycelia were extracted with water at pH 10.5. This extract (550 ml) was purified over a column packed with 100 ml of HP-20 as described in Example 2 to give a lyophilized crude product (190 mg). A portion of this product (100 mg), dissolved in 5 ml of $CH_3CN$:pyrOAc (36:64) at pH 3.6, was applied to a 300-ml glass column packed with Lichroprep RP-8 resin (25–40 μm). The column was eluted with $CH_3CN$:0.05% pyrOAc (1:4) at pH 3.6 at a flow rate of 8 ml/min. Product was detected by UV absorbance at 280 nm, by *B. subtilis* bioassay and by analytical HPLC. Fractions containing the desired activity were combined, adjusted to pH 6.5 with N NaOH, then concentrated to remove $CH_3CN$. The resulting aqueous solution (50 ml) was applied to a 40-ml column filled with 12 ml of LP1-C18 resin in water. The column was washed with water (100 ml) to remove the salt, and the active material was eluted with CH$_3$CN:H$_2$O (7:3). The eluate was concentrated and lyophilized to give 10 mg of purified antibiotic CUC/CSV.

EXAMPLE 4

Preparation of CUC/CSV by Bioconversion of Actaplanin Factor A with Culture CUC 014

Following the procedure of Example 3, but using culture CUC 014 (NRRL 15647) instead of culture CSV 558, actaplanin factor A is converted to antibiotic CUC/CSV.

EXAMPLE 5

Analytical HPLC System For Antibiotic CUC/CSV

Column: 4.6-×250-mm stainless steel
Packing: Shandon ODS Hypersil-5 micron
Solvent: CH$_3$CN:0.05M KH$_2$PO$_4$ adjusted to pH 3.2 with H$_3$PO$_4$ (21:79)
Flow Rate: 1.0 ml/min.
Detection: UV at 220 nm
Chart speed: 20 cm/hr.
Retention time: 9.3 minutes

I claim:

1. A biologically pure culture of *Actinoplanes missouriensis* NRRL 15646, or a variant or mutant thereof which, when cultured together with *Actinoplanes missouriensis* NRRL 15647, cosynthesizes antibiotic CUC/CSV.

2. The biologically pure culture of claim 1 which is NRRL 15646.

3. A biologically pure culture of *Actinoplanes missouriensis* NRRL 15647, or a variant or mutant thereof which, when cultured together with *Actinoplanes missouriensis* NRRL 15646, cosynthesizes antibiotic CUC/CSV.

4. The biologically pure culture of claim 3 which is NRRL 15647.

* * * * *